United States Patent
Farber

(10) Patent No.: US 11,291,679 B1
(45) Date of Patent: Apr. 5, 2022

(54) INJECTABLE, INFUSABLE, INSTILLABLE IVERMECTIN ADJUVANT FOR CANCER THERAPIES

(71) Applicant: MOUNTAIN VALLEY MD INC., Vaughan (CA)

(72) Inventor: Michael Farber, Livingston, NJ (US)

(73) Assignee: MOUNTAIN VALLEY MD INC., Vaughan (CA)

( * ) Notice: Subject to any disclaimer, the term of this patent is extended or adjusted under 35 U.S.C. 154(b) by 0 days.

(21) Appl. No.: 17/208,012

(22) Filed: Mar. 22, 2021

(51) Int. Cl.
*A61K 31/7048* (2006.01)
*A61K 9/00* (2006.01)
*A61K 47/26* (2006.01)
*A61K 47/69* (2017.01)

(52) U.S. Cl.
CPC ........ *A61K 31/7048* (2013.01); *A61K 9/0019* (2013.01); *A61K 47/26* (2013.01); *A61K 47/6951* (2017.08)

(58) Field of Classification Search
None
See application file for complete search history.

(56) References Cited

PUBLICATIONS

CN104208017A ,machine translation, Dec. 2014. (Year: 2014).*
FR3042412A1, machine translation, Apr. 2017. (Year: 2017).*
"SOP: Intramuscular Injections in Swine." Virginia Tech, University Veterinarian & Animal Resources, Version 1, Dec. 12, 2017 [date accessed: May 12, 2021].
"Bioequivalence of ivermectin formulations in pigs and cattle," Lifschitz et al. J. Vet. Pharmacol. Therap. 22, 27-34, 1999 [date accessed: May 5, 2021].
"SOP: Subcutaneous Injections in Swine." Virginia Tech, University Veterinarian & Animal Resources, Version 1, Dec. 12, 2017 [date accessed: May 12, 2021].
"Substance Administration for Dairy Cattle." McGill, Macdonald Campus Farm Cattle Complex, Standard Operating Procedure # DC-701[date accessed: May 12, 2021].

* cited by examiner

*Primary Examiner* — Layla D Berry
(74) *Attorney, Agent, or Firm* — Michael J. Feigin, Esq.; Feigin and Fridman LLC

(57) ABSTRACT

A pharmaceutical composition comprising Ivermectin-HPBCD complexed adjuvant formulated for injection or infusion or instillation into a subject, as well as methods for formulating and using the same. The adjuvant composition of the invention in its preferred form comprises an ivermectin-HPBCD complex wherein 1 to 3 grams of the complex is dissolved in 1 ml Tween80 combined with 9 ml sterile distilled water at a pH 6.4. Composition of the present instant invention comprising ivermectin-HPBCD complexed adjuvant formulated for administration via injection or infusion or instillation to a subject find use in treatment and/or prevention of cancer.

14 Claims, No Drawings

INJECTABLE, INFUSABLE, INSTILLABLE IVERMECTIN ADJUVANT FOR CANCER THERAPIES

FIELD OF THE DISCLOSED TECHNOLOGY

The present invention relates to a novel pharmaceutical composition of cancer-therapeutic adjuvant and in particular it relates to a stable injectable, infusible and instillable pharmaceutical composition of ivermectin adjuvant for effective cancer therapies.

BACKGROUND

Cancer is one of the most deadly threats to human health. Solid tumors are responsible for most of those deaths. Cancers metastasize and grows rapidly in an uncontrolled manner, making it difficult for the early detection and treatment. The majorities of cancer therapy methods are relatively non-selective and target tumor in malignant state. The standard treatment is definitive surgery followed by chemotherapy. Such treatment mainly aims at removing as much primary and metastatic tumor as possible in order to prevent recurrence of the tumor.

Ivermectin is a macrolide antiparasitic drug with a 16-membered ring derived from avermectin that is composed of 80% 22, 23-dihydroavermectin-B1a and 20% 22, 23-dihydroavermectin-B1b. It is a broad spectrum antiparasitic and is widely used for the treatment of many parasitic diseases such as Onchocerciasis, Elephantiasis, Scabies, and many others. The mechanism of action for Ivermectin is through the activation of glutamate-gated chloride channels in the parasite which in turn causes a large amount of chloride ion influx and neuronal hyperpolarization. This results in the release of gamma-aminobutyric acid (GABA) to destroy nerves and the nerve transmission of muscle cells causes the paralysis of somatic muscles to kill parasites.

There have been many studies that have led the researchers to discover the anti-cancer characteristics and effects of Ivermectin. As we witness the rise in cost of the research and development of anticancer drugs, the concept of drug repositioning has been surfacing more often. Drug repositioning is the development of new drug indications that have been approved for clinical use. For older drugs that are widely approved for use for its original indications and have the clinical data and safety information as backup, the concept of drug repositioning enables Ivermectin to be developed via a shorter cycle and potentially lower overall development costs. The mechanism and anticancer effect of Ivermectin plays a major role in drug repositioning for cancer treatment.

In addition, Ivermectin expresses antineoplastic activity related to its ability to inhibit multidrug resistance (MDR) proteins, the AKT/mTOR pathway and blocking the Wnt/TCF pathway (transcription factor of T-cells). Ivermectin has also shown to cause the degradation of PAK-1 (p21-activated kinase), a main oncogenic kinase. It is effective in colon cancer, glioma multiforme and melanoma as well as skin and lung cancer by Wnt-TCF blocking. It can also increase the level of intracellular ROS (reactive oxygen stress) in tumor cells, associated with oxidative stress and DNA damage.

HSP27 is a molecular chaperone protein that is expressed in high levels in many cancers and often associated with drug resistance and poor prognosis. There have been studies that have discovered the potentiation of Ivermectin being used as an inhibitor of HSP27 phosphorylation to enhance the activity of anti-EGFR drugs in EGFR/HER2-driven tumors. Ivermectin combined with chemotherapeutic drugs shows great potential for cancer treatment. This combination can effectively increase efficacy, reduce toxicity, or delay drug resistance. Ivermectin already displays a variety of different mechanisms of action in different cancers and its potential for synergistic effects and enhanced efficacy in combination therapy. Since Ivermectin's various mechanism of action does not overlap with other therapies and the fact that Ivermectin has multiple targets insinuates that is not easy to produce Ivermectin resistance. Hence, there is a greater need to study and test the safe and effective combination drug therapies to maximize the anticancer effects of Ivermectin (Mingyang tang et al., 2021).

A study shows that treatment with the FDA-approved anti-parasitic drug ivermectin induces immunogenic cancer cell death (ICD) and robust T cell infiltration into breast tumors. As an allosteric modulator of the ATP/P2×4/P2×7 axis which operates in both cancer and immune cells, ivermectin also selectively targets immunosuppressive populations including myeloid cells and Tregs, resulting in enhanced Teff/Tregs ratio. While neither agent alone showed efficacy in vivo, combination therapy with ivermectin and checkpoint inhibitor anti-PD1 antibody achieved synergy in limiting tumor growth ($p=0.03$) and promoted complete responses ($p<0.01$), also leading to immunity against contralateral re-challenge with demonstrated anti-tumor immune responses. Going beyond primary tumors, this combination achieved significant reduction in relapse after neoadjuvant ($p=0.03$) and adjuvant treatment ($p<0.001$), and potential cures in metastatic disease ($p<0.001$). Statistical modeling confirmed bona fide synergistic activity in both the adjuvant ($p=0.007$) and metastatic settings ($p<0.001$). Ivermectin has dual immunomodulatory and ICD-inducing effects in breast cancer, converting 'cold' tumors 'hot', thus represents a rational mechanistic partner with checkpoint blockade. The concept of checkpoint blockade has been deemed as revolutionary approach that basically harnesses a patient's own immune system to treat cancer. But checkpoint inhibitors are only effective in subset of patients and cancer types. Recently, studies have insinuated that the efficacy of checkpoint inhibitors is primarily limited to cancers already infiltrated by T cells—often termed "hot" tumors. "Cold" tumors have little to no T cell infiltration and generally do not respond to checkpoint blockade. Triple negative breast cancer (TNBC), a subtype of breast cancer which has higher mutational load and is thought to be more "immunogenic." Even so, anti-PD1/PDL1 antibodies have produced clinical responses in only a small subset (15-20%) of TNBC patients. Hence, there has been a need to identify drugs capable of priming breast tumors (turning "cold" tumors "hot") to synergize with checkpoint blockade. Immunogenic cell death is a form of cell death that induces an immune response from the host. Immunogenic cell death is distinguished from classical apoptosis and other non-immunogenic or tolerogenic forms of cell death by several hallmarks, including release of ATP and HMGB1 and surface exposure of calreticulin. In cancer patients, ICD-based anti-tumor immune responses are linked to beneficial outcomes produced by some conventional chemotherapeutic agents. Thus, ICD-inducing chemotherapy appears to work in conjunction with the host immune system to achieve efficacy. However, chemotherapy is a double-edged sword: it can suppress as well as stimulate immune cells. An agent that induces ICD of cancer cells without suppressing immune function would be ideal for combination with checkpoint blockade. A group of scientists discovered that the anti-parasitic drug Ivermectin promotes immunogenic cell death in breast cancer cells. In previous findings there was evidence that ivermectin, an anti-parasitic drug used worldwide since 1975, modulates the P2×4/P2×7 purinergic pathway, suggesting that ivermectin may further harness tumors' intrinsic high extracellular levels of ATP for anticancer activity. Of note, P2×4/P2×7 receptors are widely expressed on various immune subpopulations, suggesting that ivermectin might also have direct immunomodulatory effects (Dobrin draganov et al., 2021).

Immunotherapy, especially checkpoint inhibition, has emerged as an effective treatment option for a range of solid tumors (1-3). Checkpoint inhibitors (CPI), such as nivolumab, are designed to harness the body's immune system to help restore antitumor immune responses. However, only a subset of patients experience deep and durable responses with CPI, highlighting a need for novel treatment approaches (4). Combinations of CPI, such as nivolumab plus ipilimumab, have incrementally improved outcomes for the treatment of melanoma, but durable responses in most patients are still limited, and the combination is associated with a greater incidence of adverse events (AE; refs. 5, 6). As low tumor PD-L1 expression, low levels of baseline tumor-infiltrating lymphocytes (TIL), and absence of a T-cell inflamed tumor microenvironment can be associated with a poor response to CPI (7-10), novel therapeutic approaches that stimulate T cells or overcome T-cell exhaustion may complement or synergize with checkpoint inhibition to achieve durable responses for more patients (Adi Diab et al., 2020).

In addition it has been shown that a chemotherapeutic adjuvant like itraconazole which is highly lipophilic and has a low and variable bioavailability is similar to that of Ivermectin exhibiting both inter- and intraindividual variations. It has also been shown that this high variability of cmax of approx. 4-5 fold in blood plasma levels results in almost 15 fold variation across the concentrations in the tumor environment (JM Poirier et al., 1996).

Accordingly, with respect to efficient dosing of a cancer-therapeutic adjuvant, it is essential to be able to accurately determine both dose onset and duration of the effect in tumor environment this cannot be done through oral dosing, therefore the solubilized injectable infusible, or instillable ivermectin product is the only viable method of providing ivermectin to the tumor environment, especially in cases such as bladder instillation for non-invasive bladder cancer or direct injection into solid tumors and for coupling with IV infusions of immunotherapeutic agents such as nivolumab, Ipilimumab, and other PD-L1 inhibitors.

However, BCG is the first line therapy for non-invasive bladder cancer but there is global shortage of BCG which has resulted in inability to treat the majority of cases with the first line therapeutic. The combination of instilled BCG with solubilized instilled Ivermectin might result in faster resolution of the tumor, complete regression over longer period of time and therefore less maintenance doses thus reducing the burden of supply so that all diagnosed case can be afforded the opportunity for first line treatment with BCG.

The present specification solves the above mentioned problems and discloses an injectable, infusible and instillable pharmaceutical composition. The pharmaceutical composition disclosed herein formulated in a manner that essentially produces an adjuvant of ivermectin complexed with 2-hydroxypropyl-β-cyclodextrin (HPBCD) in TWEEN80-water solution. The end result is an improved cancer therapy.

Hence, there remains a greater need for effective combination drug therapies to maximize the anticancer effects of ivermectin that has been solved by present instant invention.

All the problems, disadvantages and the limitations of the above-mentioned relevant and conventional arts are being overcome by the method and composition of the present instant invention, which has various technical advancements and certainly economic benefits over the conventional arts.

SUMMARY OF THE INVENTION

The objective of the present instant invention is to provide a much needed and highly effective cancer-therapeutic adjuvant by providing a solubilized injectable infusible, or instillable ivermectin product.

The present instant invention provides an injectable, infusible and instillable pharmaceutical composition disclosed herein for the treatment of cancer.

In one aspect of the present instant invention provides a new injectable, infusible and instillable ivermectin adjuvant composition and which presents comparatively superior pharmaceutical properties than previously known formulations.

In second aspect of the present instant invention provides a process for preparation of said novel injectable, infusible and instillable ivermectin adjuvant composition.

Other aspect of the present instant invention discloses in, in part, a method of preparing an novel injectable, infusible and instillable pharmaceutical composition disclosed herein. A method disclosed herein comprises the steps of:

a) preparing an ivermectin-HPBCD complex to achieve a final concentration of 11 to 15% (w/w) of ivermectin within the complex b) addition from 1 to 3 grams of complex from step a) to a mixture containing 1 ml of tween 80 and 9 ml of sterile distilled water;

c) shaking the mixture formed in step b) until total dissolution; and d) calibrating the pH of said mixture formed in step b) to pH 6.4. The abbreviation "w/w" is defined as "weight for weight" or "weight by weight", the proportion of a particular substance within a mixture, as measured by weight or mass.

Furthermore, the resulting mixture is equilibrated for 24 hours in the refrigerator in a temperature ranging from 4-8 degree Celsius. The resulting injectable, infusible and instillable pharmaceutical composition disclosed herein of ivermectin adjuvant has a shelf-life of 3-4 years.

Moreover, in one of the object of the present invention, said novel, injectable, infusible and instillable ivermectin adjuvant pharmaceutical composition can be directly injected into the solid tumors and the dosage is dependent upon the weight of the tumor.

However, in one of the object of the present invention, said novel, injectable, infusible and instillable ivermectin adjuvant pharmaceutical composition can be infused by intravenous method at a dosage of 400 ug/Kg.

Other features and advantages of the present instant invention will be apparent from the detailed description, and from the appended claims. Thus, other aspects of the present instant invention are described in the following disclosure and are within the ambit of the present instant invention.

DESCRIPTION OF EMBODIMENTS OF THE DISCLOSED TECHNOLOGY

In the following description, certain specific details are set forth in order to provide a thorough understanding of various embodiments of the present instant invention. However, one skilled in the art will understand that the invention is not limited to the embodiments described herein, and are not intended to represent the scale of the various embodiments. It should be understood that the detailed description are not intended to limit the invention to the particular form disclosed, but on the contrary, the invention is to cover all modifications, equivalents, and alternatives falling within the scope of the present instant invention as defined by the appended claims. As used throughout this description, the word "may" is used in a permissive sense (i.e. meaning having the potential to), rather than the mandatory sense, (i.e. meaning must). Further, the words "a" or "an" mean "at least one" and the word "plurality" means "one or more" unless otherwise mentioned.

In this specification, whenever a composition or an element or a group of elements is preceded with the transitional phrase "comprising", it is understood that we also contemplate the same composition, element or group of elements with transitional phrases "consisting of", "consisting", "selected from the group of consisting of, "including", or "is" preceding the recitation of the composition, element or group of elements and vice versa.

Unless the context requires otherwise, throughout the present specification and claims, the word "comprise" and variation thereof, such as, "comprises" and "comprising" are to be construed in an open, inclusive sense that is as "including, but not limited to".

Reference throughout this specification to "one embodiment" or "an embodiment" means that a particular feature, structure or characteristic described in connection with the embodiment is included in at least one embodiment of the present instant invention. Thus, the appearances of the phrases "in one embodiment" in various places throughout this specification are not necessarily all referring to the same embodiment. Furthermore, the particular features, structures, or characteristics may be combined in any suitable.

The present invention relates to a novel pharmaceutical composition of cancer-therapeutic adjuvant and in particular it relates to a solubilized injectable, infusible and instillable pharmaceutical composition of ivermectin adjuvant for effective cancer therapies.

In one of the embodiments the present instant invention describes a new injectable, infusible and instillable ivermectin adjuvant composition and which presents comparatively superior pharmaceutical properties than previously known formulations.

In another embodiment of the present instant invention discloses a method for preparation of said novel injectable, infusible and instillable ivermectin adjuvant composition.

Moreover, in another embodiment of the present instant invention discloses an injectable, infusible and instillable pharmaceutical composition that comprises ivermectin to achieve a final concentration of about 1 to 3% (w/w). Further, 1 to 3 grams of ivermectin-2-hydroxypropyl-β-cyclodextrin (HPBCD) complex is dissolved in 1 ml tween 80 added to 9 ml sterile distilled water and then the pH is adjusted to 6.4. The resulting mixture is equilibrated for 24 hours in the refrigerator in a temperature ranging from 4-8 degree Celsius. The resulting injectable, infusible and instillable pharmaceutical composition of ivermectin adjuvant has a self-life of 3-4 years.

Furthermore, in one of the embodiments of the present instant invention, said novel, injectable, infusible and instillable ivermectin adjuvant pharmaceutical composition can be directly injected into the solid tumors and the dosage is dependent upon the weight of the tumor.

However, in another embodiment of the present instant invention, said novel, injectable, infusible and instillable ivermectin adjuvant pharmaceutical composition can be infused by intravenous method at a dosage of 400 ug/Kg.

In one set of embodiments the pharmaceutical composition describes a process for the preparation of an injectable ivermectin adjuvant pharmaceutical composition comprising the steps of:
  a) preparing an ivermectin-HPBCD complex to achieve a final concentration of 11 to 15% (w/w) of ivermectin within the complex
  b) adding from 1 to 3 grams of mixture from step a) to a 1 ml tween 80 combined with 9 ml of sterile distilled water;
  c) shaking said mixture formed in step b) until total dissolution; and
  d) calibrating the pH of said mixture formed in step b) to pH 6.4.

In another embodiment of the present instant invention, the ivermectin adjuvant pharmaceutical composition is further equilibrated for about 24 hours in a refrigerator maintained in a temperature ranging from 4-8 degree Celsius. The present invention as described above through embodiments discussed above, offer several advantages. For example, the present instant invention provide an effective combination drug therapy to maximize the anticancer effect of ivermectin.

As to the manner of usage and operation of the instant invention, same should be apparent from the above disclosure, and accordingly no further discussion relevant to the manner of usage and operation of the instant invention shall be provided.

Therefore, the foregoing is considered illustrative of only the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Any device or step to a method described in this disclosure can comprise or consist of that which it is a part of, or the parts which make up the device or step. The term "and/or" is inclusive of the items which it joins linguistically and each item by itself. "Substantially" is defined as "at least 95% of the term being described" and any device or aspect of a device or method described herein can be read as "comprising" or "consisting" thereof.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalence of the claims are to be embraced within their scope. Combinations of any of the methods, systems, and devices described herein-above are also contemplated and within the scope of the disclosed technology.

What is claimed is:

1. An ivermectin adjuvant pharmaceutical composition comprising:
  an ivermectin-HPBCD complex, wherein
    the complex comprises 11% to 15% (w/w) ivermectin, wherein 1 to 3 grams of the complex is dissolved in 1 ml polysorbate 80 and added to 9 ml sterile distilled water, and wherein the pH of the composition is 6.4, wherein said composition is administrable via injection, infusion and/or instillation to a subject.

2. The ivermectin adjuvant pharmaceutical composition of claim 1, wherein said composition is administrable for the treatment and/or prevention of cancer.

3. The ivermectin adjuvant pharmaceutical composition of claim 1, wherein said composition is directly administrable into a solid tumor.

4. The ivermectin adjuvant pharmaceutical composition of claim 3, wherein said composition is administrable in a dosage based on a weight of said solid tumor.

5. The ivermectin adjuvant pharmaceutical composition of claim 1, wherein said composition is intravenously administrable.

6. The ivermectin adjuvant pharmaceutical composition of claim 5, wherein said composition is administrable in a dosage of 400 μg/Kg.

7. A process for the preparation of an ivermectin adjuvant pharmaceutical composition comprising the steps of:

preparing an ivermectin-HPBCD complex, wherein the complex comprises 11% to 15% (w/w) ivermectin;

adding from 1 to 3 grams of the complex from step a) to 1 ml polysorbate 80 forming a solution;

adding 1 ml of solution from step b) to 9 ml sterile distilled water to form a mixture;

shaking said mixture formed in step c) until total dissolution; and calibrating the pH of said mixture formed in step d) to 6.4, wherein said composition is administrable via injection, infusion and/or instillation to a subject.

8. The process according to claim 7, wherein said ivermectin adjuvant pharmaceutical composition is prepared by equilibration of said mixture formed in step e) for 24 hours in a refrigerator maintained in a temperature range of 4-8 degree Celsius.

9. The process according to claim 7, wherein said ivermectin adjuvant pharmaceutical composition has a shelf-life in the range between 3-4 years.

10. The process according to claim 7, wherein said composition is administrable for the treatment and/or prevention of cancer.

11. The process according to claim 7, wherein said composition is directly administrable into a solid tumor.

12. The process according to claim 11, wherein said composition is administrable in a dosage based on a weight of said solid tumor.

13. The process according to claim 7, wherein said composition is intravenously administrable.

14. The process according to claim 13, wherein said composition is administrable in a dosage of 400 μg/Kg.

* * * * *